United States Patent [19]

Salomonsson et al.

[11] Patent Number: 4,520,670

[45] Date of Patent: Jun. 4, 1985

[54] METHOD AND APPARATUS FOR GENERATING SHORT ULTRASONIC ECHO PULSES

[76] Inventors: Göran Salomonsson, Lagerbrings väg 7 C, S-222 51 Lund; Per O. Börjesson, Nygård, S-290 71 Mörrum; Bengt Mandersson, Magistratsvägen 29, S-222 43 Lund; Nils-Gunnar Holmer, Gilleskroken 7, S-222 47 Lund; Kjell Lindström, N. Skogsvägen 3, S-236 00 Höllviksnäs, all of Sweden

[21] Appl. No.: 527,576

[22] PCT Filed: Dec. 20, 1982

[86] PCT No.: PCT/SE82/00431

§ 371 Date: Aug. 18, 1983

§ 102(e) Date: Aug. 18, 1983

[87] PCT Pub. No.: WO83/02330

PCT Pub. Date: Jul. 7, 1983

[30] Foreign Application Priority Data

Dec. 22, 1981 [SE] Sweden .................................. 8107731

[51] Int. Cl.³ ............................................. G01N 29/04

[52] U.S. Cl. ........................................ 73/602; 73/642; 73/632

[58] Field of Search ................. 73/602, 642, 596, 632; 367/137

[56] References Cited

U.S. PATENT DOCUMENTS 4,271,705 6/1981 Crostack ............................. 73/602

Primary Examiner—Anthony V. Ciarlante
Attorney, Agent, or Firm—Trexler, Bushnell & Wolters, Ltd.

[57] ABSTRACT

A method and an apparatus for generating short ultrasonic echo pulses by means of an ultrasonic transducer (2) utilizes a shift register (6) for storing a signal for excitation of said ultrasonic transducer. The stored signal is a weighted least squares filter signal to the transducer proper and is supplied to said transducer via a digital-to-analogue converter (7). Repeated adjustment of the stored signal can be effected by supplying, via an analogue-to-digital converter (11), the echo pulse signals from the ultrasonic transducer to a logic unit (12) for analysis.

8 Claims, 8 Drawing Figures

METHOD AND APPARATUS FOR GENERATING SHORT ULTRASONIC ECHO PULSES

The present invention relates to a method and an apparatus for generating short ultrasonic pulses.

Ultrasonic echo pulses are widely used nowadays in medical diagnosis. This diagnostic technique is based upon reflections of ultrasonic energy from boundary surfaces between media having different acoustic impedance. The time interval or delay between the emission of a pulse and the reception of an echo is a measure of the distance from the ultrasonic emitter/receiver (transducer) to the reflecting surface. Thus, the same transducer is usually employed for both emission and reception.

Sound is propagated in water and in soft human tissue at a velocity of about 1500 m/s, for which reason an echo delay of 1 μs corresponds to a distance of about 0.75 mm. To be able to distinguish echo pulses from adjacent boundary surfaces, the echo pulses thus must be short and well-defined. The axial resolution in the ultrasonic echo method thus is strongly dependent on the duration of the impulse response of the ultrasonic transducer.

It has previously been endeavoured to improve the mechanical construction of the ultrasonic transducer, and also a special signal processing of the received echo pulse signals immediately before the detection proper was introduced in order to determine the distances to the boundary surfaces. For example, the signal processing utilized has comprised the analogue or digital inverse filtration of the electric signals emitted by the transducer in response to received echo pulse signals. However, the results obtained with this technique have not been entirely satisfactory, inter alia because the impulse response of the ultrasonic transducer has a narrow bandpass characteristic so that it is difficult to devise suitable inverse filters.

According to the invention, short ultrasonic pulses are generated by imparting to the method and the apparatus the special features which are stated in the appended claims.

The invention will be described in more detail in the following, reference being had to the accompanying drawings.

Figure 1:
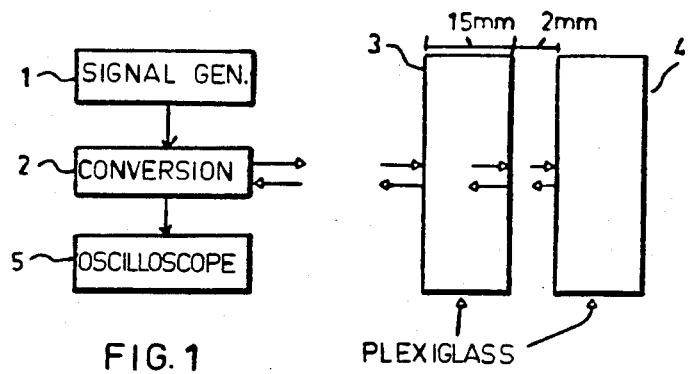
FIG. 1 illustrates the basic principle of this invention in an apparatus according to the invention directed towards a specific test object.

The apparatus according to the invention, as shown in FIG. 1, comprises a signal generator 1 which is coupled to an ultrasonic transducer 2 for the excitation thereof. In the example illustrated in FIG. 1, the ultrasonic emitter 2 emits its pulses in a water tank towards two blocks 3, 4 of plexiglass, each having a thickness of 15 mm and being spaced apart a distance of 2 mm. It should be mentioned in this connection that the velocity of sound in plexiglass is twice as high as in water, or approximately 3000 m/s.

According to the present invention, the signal generator 1 is adapted to generate an excitation signal which substantially constitutes a weighted least squares signal to the transducer proper. More particularly, this excitation signal is generated preferably by means of a pulse shaping filter which preshapes the excitation signal to the ultrasonic transducer 2.

Figure 2A:
FIGS. 2a and 2b show the impulse response and the associated frequency function of an ultrasonic transducer.
Figure 2B:
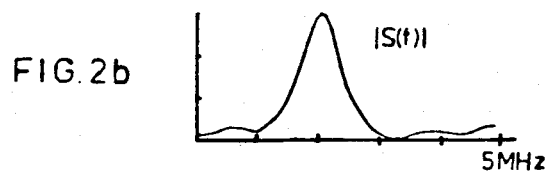

FIG. 2a shows an Example of the impulse response s(t) for an ultrasonic transducer 2 having a centre frequency of about 2 MHz. The corresponding frequency spectrum is shown in FIG. 2b illustrating the narrow bandpass characteristic typical of an ultrasonic transducer.

Figure 5A:
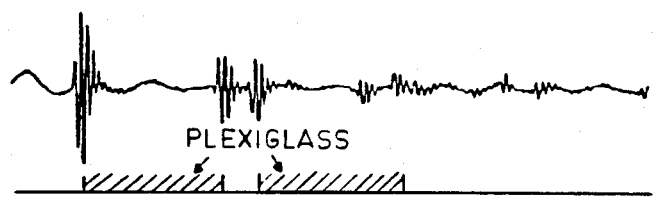
FIGS. 5a and 5b show examples of echo signals obtained respectively without and with preshaping of the excitation pulse of the ultrasonic transducer.

Upon conventional excitation of the ultrasonic transducer 2 with a rectangular pulse, an echo signal of the type shown in FIG. 5a is obtained, and this signal can be observed for instance on an oscilloscope 5 connected to the ultrasonic transducer 2.

Figure 3A:
FIGS. 3a and 3b show the impulse response and frequency characteristic of a pulse shaping filter of the weighted least squares type.
Figure 5B:
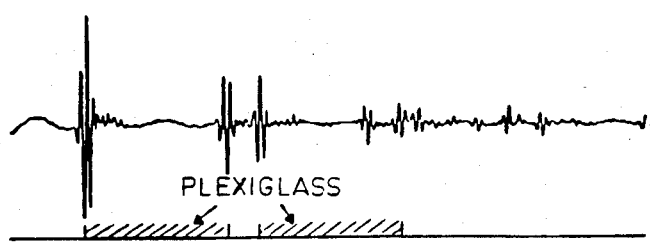

If the excitation signal of the ultrasonic transducer 2 instead is given the shape u(t) which is shown in FIG. 3a, an echo signal of the shape shown in FIG. 5b is obtained. A comparison of FIG. 5b with FIG. 5a clearly shows the improved resolution that is obtained by utilising the excitation signal according to the invention instead of the conventional rectangular pulse.

More particularly, the signal shown in FIG. 3a constitutes the impulse response from a weighted least squares filter (WLS filter).

Figure 3B:
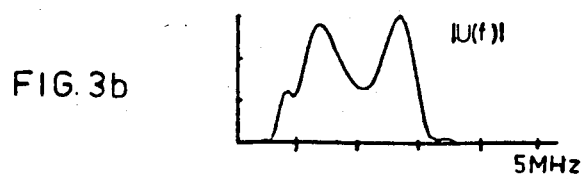

The frequency characteristic of the WLS filter is shown in FIG. 3b.

The WLS filter may be defined as a filter which minimises a cost function of the form $$I = \sum_t \{w(t) \cdot [s(t) * u(t) - \delta(t)]\}^2 + w_o \sum_t (u(t'))^2$$

in which w is a weighting parameter defined by $$w(t) \cdot \begin{cases} 0 & |t| \leq T \text{ and } t \neq 0 \\ 1 & t = 0 \text{ or } |t| > T \end{cases}$$

s(t) is the impulse response of the ultrasonic transducer, u(t) is the impulse response of the WLS filter $$\delta(t) = \begin{cases} 1 & t = 0 \\ 0 & t \neq 0 \end{cases}$$

$w_o$ is the expected noise effect

T is a resolution parameter and

\* indicates convolution.

In designing the WLS filter, the resolution parameter T and the parameter $w_o$ which pays regard to the input signal noise, must be determined. However, these parameters affect the filter independently of one another.

It should be mentioned in the context that the WLS filter is related both to the pure inverse filter and to the signal-adapted filter. Actually, these two filters are special cases of the WLS filter. The pure inverse filter is obtained by defining both $w_o$ and T as 0. The signal-adapted filter is obtained by selecting a large value for either T or $w_o$. The WLS filter satisfying the above-mentioned minimising requirements of the cost function also is the filter which best satisfies the three requirements that the echo output signal from the ultrasonic transducer is to have a high amplitude at a point, for example for t=0, that the same output signal amplitude must be low outside the resolution interval, i.e. $|t|>T$, and that the signal noise must be low.

Figure 4:
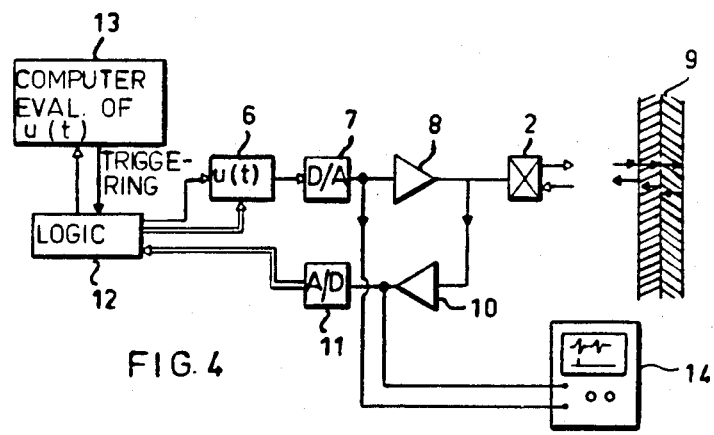
FIG. 4 is a block diagram of a test equipment incorporating the invention.

As will appear from the above, a WLS filter introduced into the signal generator 1 will improve the axial resolution of the received echo signal. FIG. 4 illustrates a test equipment for producing a suitable impulse response u(t) for preshaping the excitation pulse. This equipment comprises a shift register 6 for digital storage of the impulse response of the WLS filter. The output of the shift register 6 is coupled, via a digital-to-analogue converter 7 and a power amplifier 8, to the input of the ultrasonic transducer 2. The transducer 2 emits its pulses towards a target 9 and receives echo signals therefrom. The echo signals converted into electrical form by the transducer 2 are supplied, via a preamplifier 10 and an analogue-to-digital converter 11, to a logic unit 12. By means of a computer 13 connected to the logic unit 12, the echo signal can be evaluated, and the impulse response u(t) stored in the shift register 6 can be adjusted. For monitoring the excitation signal and the echo signal, FIG. 4 shows an oscilloscope 14 connected to the output of the converter 7 and the input of the converter 11.

Obviously, it is possible, with an apparatus devised in analogy with the test equipment according to FIG. 4, to carry out repeated adjustment of the excitation signal by inserting the resulting echo signals in some suitable algorithm.

As an alternative of the shift register 6, it is possible to utilise, for example, a programmable read-only memory (PROM) or the like in which the suitable filter signal may thus be stored digitally.

It will be appreciated that numerous modifications of the embodiments described can be effected within the scope of this invention.

We claim:

1. A method for generating short ultrasonic echo pulses by means of an ultrasonic transducer, wherein the ultrasonic transducer is excited by means of a signal which substantially is a weighted least squares filter signal to the transducer proper.

2. A method as claimed in claim 1, characterised in that the least squares filter function of the transducer is calculated repetitively for repeated adjustment of the excitation signal of the transducer.

3. A method as claimed in claim 2, characterised in that the excitation signal is stored in digital form in a shift register and supplied to the ultrasonic transducer via a digital-to-analogue converter.

4. A method as claimed in claims 2 or 3, characterised in that the ultrasonic echo pulses received by the ultrasonic transducer are compared with desired signal pulses, and that the difference signal is utilised for adjusting the excitation signal.

5. An apparatus for generating short ultrasonic echo pulses including an ultrasonic transducer (2) having an excitation input, and a signal generator (1) connected to the excitation input of the ultrasonic transducer (2), by means adapted to generate an excitation signal which substantially is a weighted least squares filter signal.

6. An apparatus as claimed in claim 5, wherein the adapted means comprises a shift register (6) in which the excitation signal is stored in digital form, and a digital-to-analogue converter (7) connecting the output of the shift register with the excitation input of the ultrasonic transducer (2).

7. An apparatus as claimed in claim 6, and further including an analogue-to-digital converter (11) connected to the ultrasonic transducer (2) for receiving electrical signals corresponding to ultrasonic echo pulses and for converting said electrical signals into digital form for repeated adjustment of the excitation signal.

8. An apparatus as claimed in claim 5, including a read-only memory in which the excitation signal is stored in digital form.

* * * * *